(12) United States Patent
Hung et al.

(10) Patent No.: US 9,770,199 B2
(45) Date of Patent: Sep. 26, 2017

(54) FINGERPRINT IDENTIFICATION APPARATUS AND METHOD CAPABLE OF SIMULTANEOUSLY IDENTIFYING FINGERPRINT AND OXYGEN SATURATION

(71) Applicant: Gingy Technology Inc., Hsinchu (TW)

(72) Inventors: Chun-Lang Hung, Hsinchu (TW); Jen-Chieh Wu, Hsinchu (TW)

(73) Assignee: Gingy Technology Inc., Hsinchu (TW)

( * ) Notice: Subject to any disclaimer, the term of this patent is extended or adjusted under 35 U.S.C. 154(b) by 114 days.

(21) Appl. No.: 14/978,237

(22) Filed: Dec. 22, 2015

(65) Prior Publication Data

US 2016/0180139 A1    Jun. 23, 2016

(30) Foreign Application Priority Data

Dec. 22, 2014  (TW) .............................. 103144744 A (51) Int. Cl.
| | |
|---|---|
| *G06K 9/00* | (2006.01) |
| *A61B 5/1455* | (2006.01) |
| *A61B 5/1172* | (2016.01) |
| *A61B 5/00* | (2006.01) |
| *G06K 9/20* | (2006.01) |

(52) U.S. Cl.
CPC ........ *A61B 5/14552* (2013.01); *A61B 5/1172* (2013.01); *A61B 5/6826* (2013.01); *G06K 9/00087* (2013.01); *G06K 9/00107* (2013.01); *G06K 9/2018* (2013.01)

(58) Field of Classification Search
CPC ........................................................ G06K 9/00
See application file for complete search history.

(56) References Cited

U.S. PATENT DOCUMENTS

| | | | | |
|---|---|---|---|---|
| 5,719,950 | A * | 2/1998 | Osten ................... | A61B 5/0205 340/5.82 |
| 6,255,641 | B1 * | 7/2001 | Johnson ............... | A61B 5/1172 250/208.1 |
| 6,643,531 | B1 * | 11/2003 | Katarow .............. | A61B 5/1172 600/323 |
| 8,408,471 | B2 * | 4/2013 | Kim .................... | G06K 19/0718 235/380 |
| 9,298,317 | B2 * | 3/2016 | Chou .................. | G06K 9/00026 |
| 2009/0043180 | A1 * | 2/2009 | Tschautscher ....... | A61B 5/1172 600/323 |

(Continued)

*Primary Examiner* — Anand Bhatnagar
(74) *Attorney, Agent, or Firm* — Jianq Chyun IP Office (57) ABSTRACT

A fingerprint identification method capable of simultaneously identifying fingerprint image and oxygen saturation is provided. The method may include allowing for a finger to be placed on a light reception surface of a photoelectron sensor module, enabling emission of an invisible light and a visible light, receiving light intensity signals corresponding to the invisible light penetrated into the finger and then reflected by the finger and the visible light reflected from the finger using the photoelectron sensor module, converting the light intensity signals to photocurrent signals by the photoelectron sensor module, converting the photocurrent signals to a corresponding first digital signal and a second digital signal by an analog/digital converting module, and outputting a fingerprint image corresponding to the first digital signal and a finger oxygen saturation image corresponding to the second digital signal by the processor module.

9 Claims, 5 Drawing Sheets

(56) References Cited

U.S. PATENT DOCUMENTS

| | | | |
|---|---|---|---|
| 2010/0328034 A1* | 12/2010 | Medina | A61B 5/14551 340/5.83 |
| 2011/0141299 A1* | 6/2011 | Masten | G01J 3/2803 348/222.1 |
| 2014/0168167 A1* | 6/2014 | Chou | G06K 9/00026 345/175 |
| 2015/0185954 A1* | 7/2015 | Chang | G06F 3/0416 345/173 |
| 2015/0235071 A1* | 8/2015 | Chang | G06K 9/00033 382/124 |
| 2015/0379323 A1* | 12/2015 | Erhart | H04N 5/23219 382/124 |

* cited by examiner

FINGERPRINT IDENTIFICATION APPARATUS AND METHOD CAPABLE OF SIMULTANEOUSLY IDENTIFYING FINGERPRINT AND OXYGEN SATURATION

CROSS REFERENCE TO RELATED APPLICATION

This application also claims priority to Taiwan Patent Application No. 103144744 filed in the Taiwan Patent Office on Dec. 22, 2014, the entire content of which is incorporated herein by reference.

BACKGROUND

Technical Field

The present disclosure relates to a fingerprint identification apparatus and method, in particular, to a fingerprint identification apparatus and method capable of simultaneously identifying fingerprint image and oxygen saturation.

Description of Related Art

The so-called fingerprint recognition/identification as the name suggests is the use of unique fingerprint identification information on the human finger. One typical fingerprint identification apparatus may feature two elements, one of which is fingerprint sensor to collect a complete fingerprint image and the other is fingerprint algorithm. When the original fingerprint image is captured by the fingerprint sensor, the captured will be processed by the fingerprint algorithm including the extraction of fingerprint features to generate a fingerprint template before having the original fingerprint image discarded. With the fingerprint template, fingerprint comparison could be performed.

Traditionally, capacitive fingerprint sensor and optical fingerprint sensor could be used. Among the capacitive fingerprint sensors, RF capacitive sensing, pressure sensing, and thermal sensing are widely employed. The capacitive fingerprint sensor could have miniaturized sensors such as densely disposed pressure sensors or capacitance sensors integrated within a chip. When the surface of the chip is pressed by the finger, the internal micro capacitance sensors depending on different amount of charges or difference in temperature because of the aggregation of fingerprint valleys or ridges could forming the fingerprint image.

Despite the capacitive sensors are compact in size and therefore suitable to be incorporated into one portable device, manufacturing cost and durability could be disadvantages to be taken into account. Specifically, for the capacitive sensors to maintain their size (surface) for the press of the finger, certain area of the whole wafer may be cut, increasing the manufacturing cost of the capacitive sensors. Furthermore, due to the capacitive sensors could be uncapped semiconductor chips environmental factors such as sweat could damage the sensors and the capacitive sensors are prone to static charges, seriously undermining durability of such sensors and shortening operational life of the same. To minimize the impact associated with the environmental factors, certain capacitive sensors could have a layer of sapphire substrates attached to their surface for protection, undoubtedly increasing the cost in manufacturing.

Optical sensors, meanwhile, as the most primitive option to capture the fingerprint, include a light source, a dispersive prism, and a charge-coupled device (CCD). When the finger presses the dispersive prism, the fingerprint image could be obtained based on the absorption and even destruction of the total reflection by the fingerprint valleys and the fingerprint ridges. The fingerprint image could be extracted and outputted by CCD. At the time of the capture of the fingerprint, the finger is pressed upon optical elements such as acrylic or glass rather than the chip having the sensor itself. Thus, the optical sensors could be relatively inexpensive and durable. But the optical sensors are disadvantageous in its size and the complexity of assembly, rendering difficult for such sensors to be used within the portable device.

In addition, some perpetrators have used fake finger in silicone trying to get around the identification process. Such fake fingers could virtually emulate the real fingers with fingerprint and capillaries. Therefore, with the fake fingers to press the conventional fingerprint identification devices the characteristics created by the silicone such as the deformation and the fingerprint could be indistinguishable from the viewpoint of the traditional devices, resulting in the loophole in identification.

Therefore, the present disclosure could be solving the problems associated with the conventional capacitive fingerprint sensors and the optical sensors.

SUMMARY OF THE DISCLOSURE

Since the capacitive fingerprint sensors are susceptible to the environmental static charges and subject to expensive manufacturing cost, and the optical sensors are too large in size to be incorporated into the portable devices, not durable and shorter in operational life, along with the challenge facing the above fingerprint sensors that the fake finger made by silicone could easily get around the identification process, the present disclosure could offer one viable option. The fingerprint identification apparatus could identify the fingerprint image and oxygen saturation at the same time, be compact in size, not be negatively affected by the environmental factors, be with the reduced manufacturing cost, and prevent the fake fingers from getting around the identification procedure.

A fingerprint identification apparatus capable of simultaneously identifying a fingerprint image and oxygen saturation to identify fingerprint pattern and blood oxygen of a finger is disclosed. Such method may include a first light-emitting element to emit an invisible light to the finger, a second light-emitting element to emit a visible light to the finger, and a photoelectron sensor module having a light reception surface on which the finger is placed. The photoelectron sensor module may receive a first photo intensity signal of the invisible light reflected from the finger and convert the first photo intensity signal to a first photocurrent signal, and the photoelectron sensor module may also receive a second photo intensity signal of the invisible light reflected from the finger and convert the second photo intensity signal to a second photocurrent signal.

The fingerprint identification apparatus of the present disclosure may also include an analog/digital converting module electrically connected to the photoelectron sensor module, for converting the first photocurrent signal to a first digital signal and converting the second photocurrent signal to a second digital signal. The fingerprint identification apparatus of the present disclosure may further include a processor module electrically connected to the analog/digital converting module for outputting a fingerprint image corresponding to the first digital signal to be recognized and outputting a finger oxygen saturation image corresponding to the second digital signal to be recognized.

The present disclosure further provides a fingerprint identification method capable of simultaneously identifying fingerprint image and oxygen saturation. The disclosed method may include allowing for a finger to be placed on a light reception surface of an photoelectron sensor module, enabling a first light-emitting element to emit an invisible light to the finger and enabling a second light-emitting element to emit a visible light to the finger, receiving a first light intensity signal corresponding to the invisible light penetrated into the finger and then reflected by the finger using the photoelectron sensor module and receiving a second light intensity signal corresponding to the visible light reflected from the finger using the photoelectron sensor module, converting the first light intensity signal to a first photocurrent signal by the photoelectron sensor module, converting the second light intensity signal to a second photocurrent signal by the photoelectron sensor module, and delivering the first photocurrent signal and the second photocurrent signal to an analog/digital converting module by the photoelectron sensor module, converting the first photocurrent signal to a corresponding first digital signal by the analog/digital converting module, converting the second photocurrent signal to a corresponding second digital signal by the analog/digital converting module, and delivering the first digital signal and the second digital signal to a processor module by the analog/digital converting module, and outputting a fingerprint image corresponding to the first digital signal by the processor module, outputting a finger oxygen saturation image corresponding to the second digital signal by the processor module, and recognizing the fingerprint image and the finger oxygen saturation image by the processor module.

Another fingerprint identification method in the present disclosure may include allowing for a finger to be placed on a light reception surface of an photoelectron sensor module, enabling a first light-emitting element to emit an invisible light to the finger, receiving a first light intensity signal corresponding to the invisible light penetrated into the finger and then reflected by the finger using the photoelectron sensor module, converting the first light intensity signal to a first photocurrent signal by the photoelectron sensor module and converting the first photocurrent signal to a corresponding first digital signal by an analog/digital converting module, processing the first digital signal to prepare a fingerprint image to be recognized by a processor module and upon the authentication of the fingerprint image is recognized enabling a second light-emitting element to emit a visible light to the finger, and receiving a second photo intensity signal of the visible light reflected from the finger by the photoelectron sensor module, converting the second photo intensity signal to a second photocurrent signal by the photoelectron sensor module and delivering the second photocurrent signal to the analog/digital converting module, converting the second photocurrent signal to a second digital signal by the analog/digital converting module, and outputting a finger oxygen saturation image by the processor module on basis of the second digital signal to determine whether a real finger is placed.

The present disclosure may employ the photoelectron sensor module to receive the visible light and the invisible light penetrating into and reflected from the finger, and simultaneously identify the fingerprint image and the oxygen saturation image of the finger to avoid the identification from being bypassed by the fake finger, which could significantly enhance the performance of the identification process. Further, because of the photoelectron sensor module being compact as one of its advantages, the fingerprint identification apparatus of the present disclosure may be incorporated into the portable devices. The present disclosure may effectively isolate optical and electrical sensing, minimizing the impact arising out of the environmental static charges and eliminating the need of the sapphire substrate functioning as the protection to reduce the cost in manufacturing.

For further understanding of the present disclosure, reference is made to the following detailed description illustrating the embodiments and examples of the present disclosure. The description is only for illustrating the present disclosure, not for limiting the scope of the claim.

BRIEF DESCRIPTION OF THE DRAWINGS

The drawings included herein provide further understanding of the present disclosure. A brief introduction of the drawings is as follows.

DESCRIPTION OF THE EXEMPLARY EMBODIMENTS

The aforementioned and other technical contents, features, and efficacies will be shown in the following detail descriptions of a preferred embodiment corresponding with the reference Figures.

Figure 1:
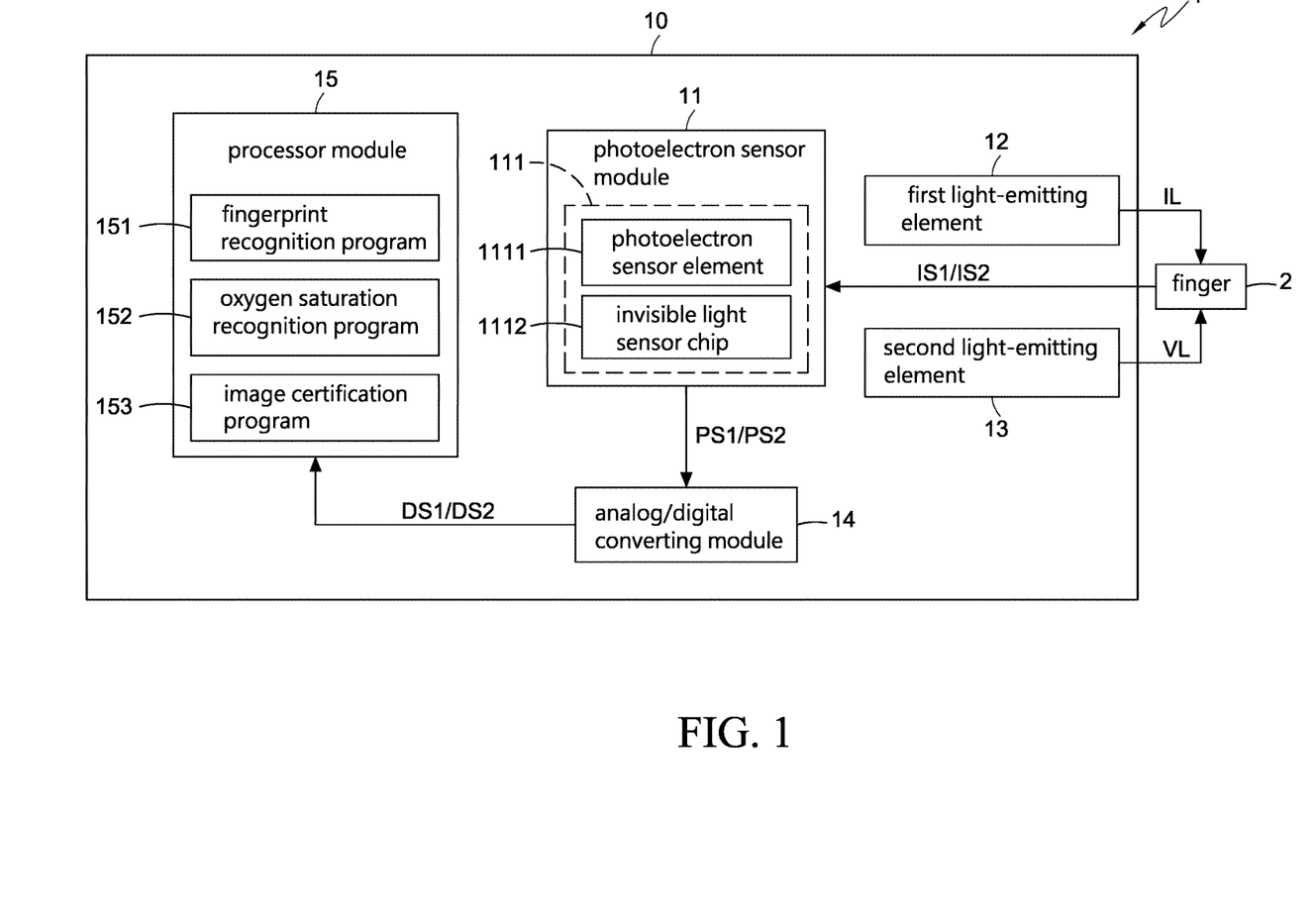
FIG. 1 is simplified block diagram of a fingerprint identification apparatus according to one embodiment of the present disclosure.
Figure 2:
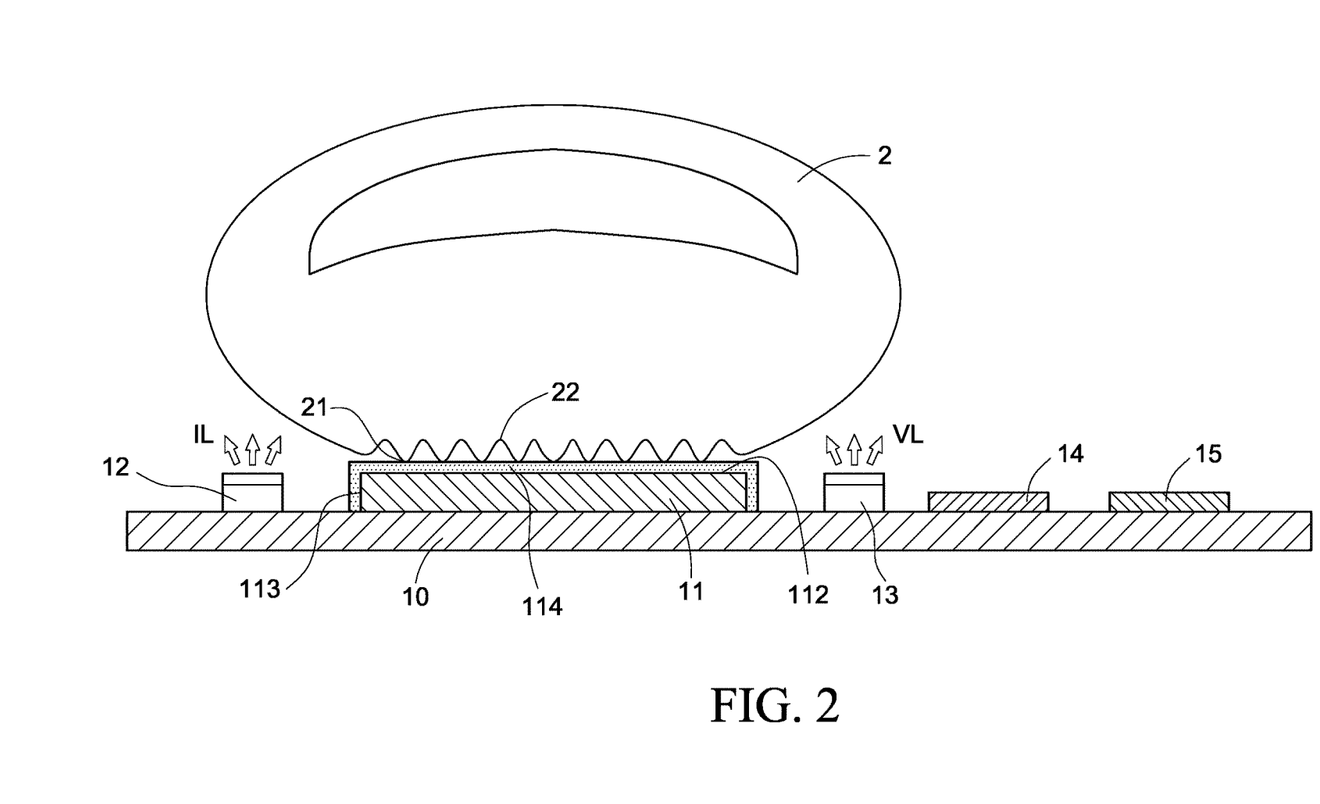
FIG. 2 is a structural diagram of a fingerprint identification apparatus according to one embodiment of the present disclosure.
Figure 3:
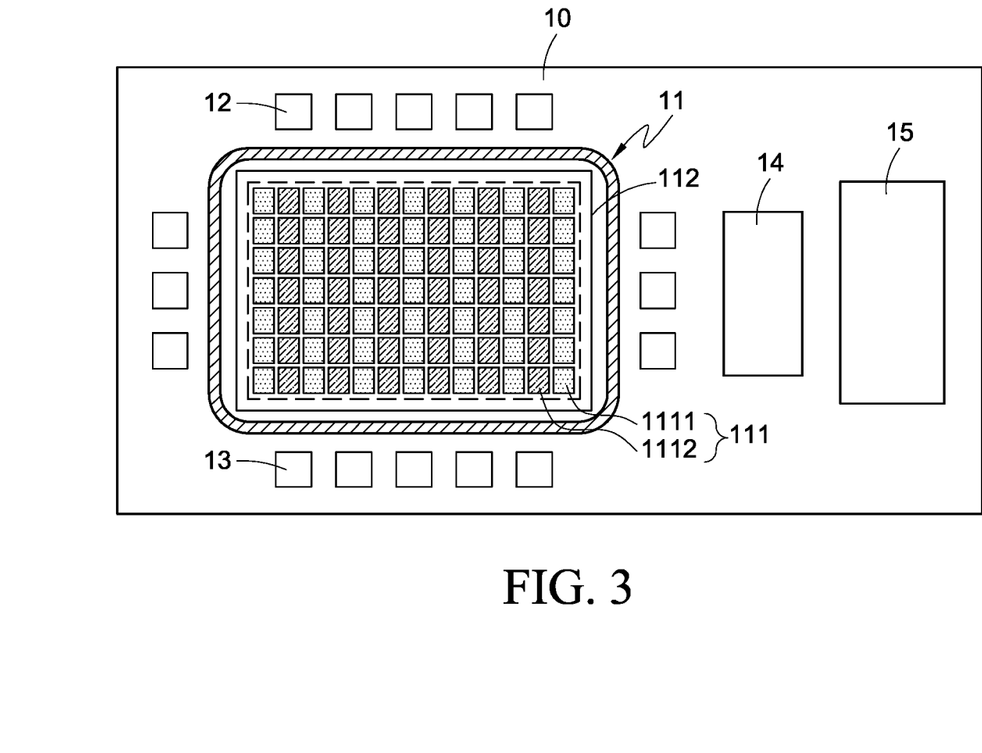
FIG. 3 is a schematic diagram of a photoelectron sensor module of the fingerprint identification apparatus according to one embodiment of the present disclosure.

Please refer to FIGS. 1-3 of a simplified block diagram showing a fingerprint recognition apparatus 1, a structural diagram of the same, and a schematic diagram of a photoelectron sensor module of the same, respectively, according to one embodiment of the present disclosure. The fingerprint recognition apparatus 1 may include a functionality circuit board 10, a photoelectron sensor module 11, a first light-emitting element 12, a second light-emitting element 13, an analog/digital converting module 14, and a processor module 15. In one implementation, the functionality circuit board 10 may allow for the photoelectron sensor 11 module, the first light-emitting element 12, and the second light-emitting element 13 to be electrically disposed thereon. In one implementation, the first light-emitting element 12 and the second light-emitting element 13 may be light-emitting diodes though the present disclosure is not therefore limited by such.

Moreover, the photoelectron sensor module 11 may be electrically coupled to the analog/digital converting module 14 and the processor module 15. In another implementation, the analog/digital converting module 14 and the processor module 15 may be electrically disposed on the functionality circuit board 10, though both the analog/digital converting module 14 and the processor module 15 may be disposed on a portable electronic device (not shown) in which case the analog/digital converting module 14 and the processor module 15 may be externally and electrically coupled to the photoelectron sensor module 11, for any further processing to be performed.

In one implementation, the photoelectron sensor module 11 may be having multiple photoelectron sensing elements 111 arranged in arrays. The photoelectron sensing elements may include visible light sensor chips 1111 and invisible light sensor chips 1112. The visible light sensor chips 1111 and the invisible light sensor chips 1112 may be adjacently arranged to define a light reception surface 112. The light reception surface 112 may be where a finger 2 is placed. The fingerprint identification apparatus 1 may further include a scattering medium 114 covering the light reception surface 112 of the photoelectron sensor module 11. In another implementation, the scattering medium 114 may cover not only the light reception surface 112 but also peripheral surfaces 113 of the photoelectron sensor module 11. As such, the scattering medium 114 may serve as an interface on which the finger 2 could be pressed. When the light from the first light-emitting element 12 and the second light-emitting element 13 enters into the scattering medium 114, the scattering medium 114 may uniformly spread the received light, functioning as one uniform surface light source and allowing for the finger 2 to receive the largest amount of the light.

The first light-emitting element 12 and the second light-emitting element 13 may adjacently surround the photoelectron sensor module 11. The first light-emitting element 12 and the second light-emitting element 13 may be packaged in one single chip or even separately disposed. When the first light-emitting element 12 and the second light-emitting element 13 are in separated chips, the corresponding light-emitting chips may be disposed on the peripheral of the photoelectron sensor module 11. The first light-emitting element 12 may be used to emit an invisible light with the wavelength ranging between 780 nm and 3000 nm as an infrared radiation. The second light-emitting element 13 may be used to emit a visible light with the wavelength ranging from 400 nm to 700 nm.

Figure 4:
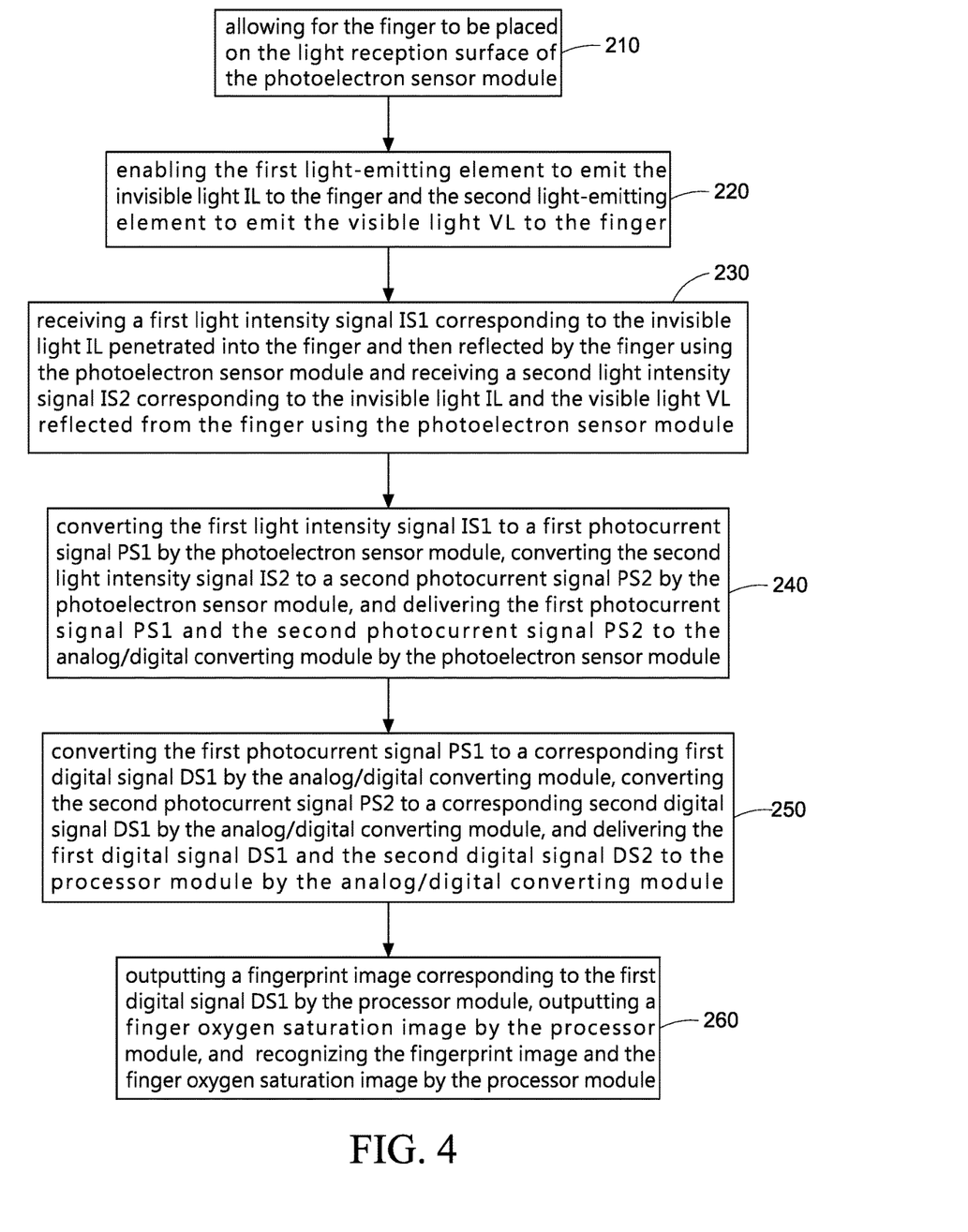
FIG. 4 is a flow chart showing a fingerprint identification method according to one embodiment of the present disclosure.

In conjunction with FIG. 1, please refer to FIG. 4 of a flow chart showing a fingerprint identification method capable of simultaneously identifying a fingerprint image and oxygen saturation of a finger according to one embodiment of the present disclosure. The method may include: (1) step 210: allowing for the finger 2 to be placed on the light reception surface 112 of the photoelectron sensor module 11, (2) step 220: enabling the first light-emitting element 12 to emit the invisible light IL to the finger 2 and the second light-emitting element 13 to emit the visible light VL to the finger 2, (3) receiving a first light intensity signal IS1 corresponding to the invisible light IL penetrated into the finger 2 and then reflected by the finger using the photoelectron sensor module 11 and receiving a second light intensity signal IS2 corresponding to the invisible light IL and the visible light VL reflected from the finger using the photoelectron sensor module 11, (4) step 240: converting the first light intensity signal IS1 to a first photocurrent signal PS1 by the photoelectron sensor module 11, converting the second light intensity signal IS2 to a second photocurrent signal PS2 by the photoelectron sensor module 11, and delivering the first photocurrent signal PS1 and the second photocurrent signal PS2 to the analog/digital converting module 14 by the photoelectron sensor module 11, (5) step 250: converting the first photocurrent signal PS1 to a corresponding first digital signal DS1 by the analog/digital converting module 14, converting the second photocurrent signal PS2 to a corresponding second digital signal DS1 by the analog/digital converting module 14, and delivering the first digital signal DS1 and the second digital signal DS2 to the processor module 15 by the analog/digital converting module 14, and (6) step 260: outputting a fingerprint image corresponding to the first digital signal DS1 by the processor module 15, outputting a finger oxygen saturation image by the processor module 15, and recognizing the fingerprint image and the finger oxygen saturation image by the processor module 15.

In step 210, the finger 2 may press the light reception surface 112 of the photoelectron sensor module 11. In another implementation, the finger 2 may press the scattering medium covering the light reception surface 112. Upon the press of the finger 2, the functionality circuit board 10 may drive the first light-emitting element 12 to emit the invisible light IL to the finger 2 while driving the second light-emitting element 13 to emit the visible light VL to the finger 2.

In step 220, the sequence of the light emitting for the first light-emitting element 12 and the second light-emitting element 13 may include the follows, though the below does not necessarily exhaust all options could be utilized. In a first mode, the first light-emitting element 12 and the second light-emitting element 13 may synchronously emit the invisible light IL and the visible light VL, respectively. In a second mode, the second light-emitting element 13 may emit the visible light VL after the first light-emitting element 12 emits the invisible light IL and receives the fingerprint image. In a third mode, both the first light-emitting element 12 and the second light-emitting element 13 may take turns in light emitting. Specifically, the first light-emitting element 12 may temporarily shut down after emitting the invisible light IL to the finger 2 at which point the second light-emitting element 13 may emit the visible light VL to the finger 2. Such alternating pattern may continue for the emitting of the invisible light IL and the visible light VL to the finger 2.

In step 230, as the surface of the finger 2 includes fingerprint valleys 21 and fingerprint ridges 22 and the fingerprint valleys 21 may be in contact with the light reception surface 112, when the invisible light IL penetrates into the finger 2 and is reflected the invisible light IL may enter into the light reception surface 112 through the fingerprint valleys 21. Accordingly, the first photo intensity signal IS1 that may be high in intensity may be obtained. On the other hand, gaps exist between the fingerprint ridges 22 and the light reception surface 112, part of the invisible light IL when penetrating out of the fingerprint ridges 22 may cause scattering and refraction before entering into the light reception surface 112. Consequently, another first photo intensity signal IS1 with reduced intensity may be obtained. With the photo intensity signals differing from each other in terms of the intensity, photo contrast between the fingerprint valleys 21 and the fingerprint ridges 22 may result.

As blood flows in the finger 2, the oxygen saturation of the blood (the percentage that blood protein and oxygen integrate) may be reflected in optical characteristics of the fingerprint. When the visible light VL is emitted to the finger 2, such visible light VL may aid the reception of the invisible light IL by oxygenated hemoglobin and de-oxy hemoglobin. In other words, the blood in arteries tend to be having more oxygenated hemoglobin in concentration may absorb extra blue light when absorbing less amount of red light. On the other hand, the blood in veins may be having more de-oxy hemoglobin in concentration and may absorb the visible light across the entire spectrum more uniformly and therefore is relatively dark blue. When the invisible light IL penetrates into the finger 2 before being reflected to the light reception surface 112, one second photo intensity signal IS2 consistent with light absorption rate for oxygenated hemoglobin and one second photo intensity signal IS2 consistent with light absorption rate for de-oxy hemoglobin may be obtained.

In step 240, the photoelectron sensor module 11 may simultaneously receive the first photo intensity signals IS1 from the fingerprint valleys 21 and the fingerprint ridges 22 and may convert the first photo intensity signals IS1 into the first photo current signals PS1. Similarly, the photoelectron sensor module 11 may simultaneously receive the second photo intensity signals IS2 corresponding to oxygenated hemoglobin and de-oxy hemoglobin in the blood before converting the second photo intensity signals IS2 to the second photo current signals PS2. The photoelectron sensor module 11 may further deliver the first photo current signals PS1 and the second photo current signals PS2 to the analog/digital converting module 14 for further processing.

It is worth noting that the photoelectron sensor module 11 may operate using photo-voltaic, photo-conductive, or photo-emissive approach. For instance, the photo-voltaic conversion may exist between junction interfacing two different materials. When the visible light VL or the invisible light IL is emitted upon the junction two output voltages associated with illumination may result at two terminals of the junction. Materials used may include semiconductor materials such as silicon, germanium, or indium antimonide for p-n junction. The photo-conductive method may rely on the semiconductor materials with less resistance when the illumination increases and becoming conductive when the materials absorb the energy carried by input photons to produce electron carriers. The photo-emissive method takes advantage of the characteristics that when the energy of the inputted light is large enough electrons may escape from their orbits. The above description for the conversion is only illustrative and therefore does not intend to limit the use of other applicable methods implementing the photoelectron sensor module 11.

In step 250, the analog/digital converting module 14 depending on the intensity of the first photo current signal PS1 may convert the same to its corresponding first digital signal DS1. Meanwhile, based on the intensity of the second photo current signal PS2 the analog/digital converting module 14 may convert the same to its corresponding second digital signal DS2. The analog/digital converting module 14 may further filter and/or amplify the first digital signal DS1 and/or the second digital signal DS2, before delivering the same to the processor module 15.

In step 260, the processor module 15 may include a fingerprint recognition program 151, an oxygen saturation recognition program 152, and an image certification program 153. The fingerprint recognition program 151 when executed may process the first digital signal DS1 for obtaining fingerprint images of the fingerprint valleys 21 (bright areas) and the fingerprint ridges 22 (dark areas) of the finger 2. The oxygen saturation recognition program 152 when executed may process the second digital signal DS2 for obtaining the finger oxygen saturation images of the finger 2 corresponding to oxygenated hemoglobin and de-oxy hemoglobin. Additionally, the image certification program when executed may ensure the user identity according to the fingerprint image and verify if the finger oxygen saturation image is from the real finger.

Figure 5:
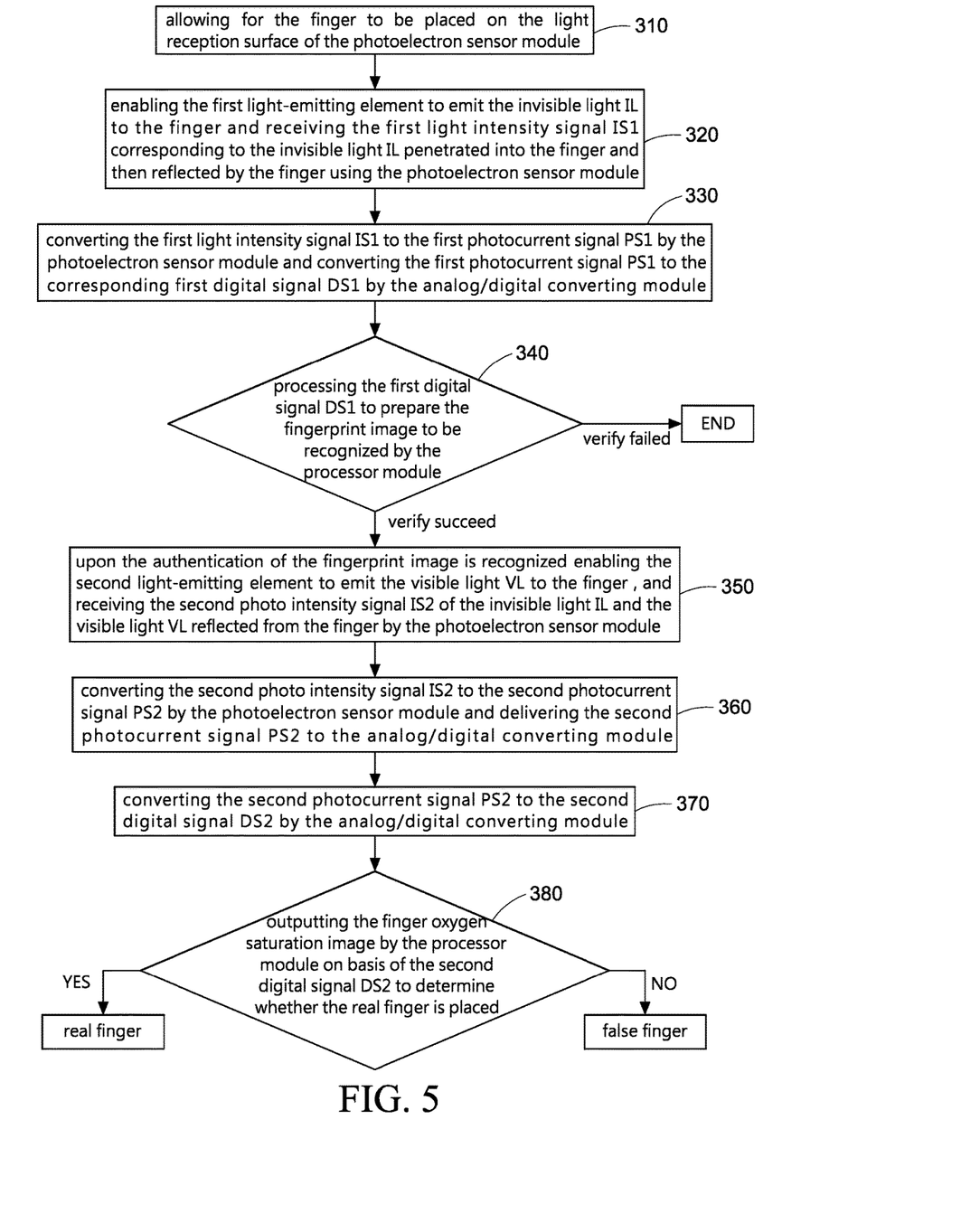
FIG. 5 is another flow chart showing another fingerprint identification method according to another embodiment of the present disclosure.

Please refer to FIG. 5 showing another flow chart of a fingerprint identification method according to another embodiment of the present disclosure. The embodiment in FIG. 5 may involve the similar hardware structures and may differ from its counterpart in FIG. 4 on certain fronts. The flow chart shown in FIG. 5 may include: (1) step 310: allowing for the finger 2 to be placed on the light reception surface 112 of the photoelectron sensor module 11, (2) step 320: enabling the first light-emitting element 12 to emit the invisible light IL to the finger 2 and receiving the first light intensity signal IS1 corresponding to the invisible light IL penetrated into the finger 2 and then reflected by the finger 2 using the photoelectron sensor module 11, (3) step 330: converting the first light intensity signal IS1 to the first photocurrent signal PS1 by the photoelectron sensor module 11 and converting the first photocurrent signal PS1 to the corresponding first digital signal DS1 by the analog/digital converting module 14, (4) step 340: processing the first digital signal DS1 to prepare the fingerprint image to be recognized by the processor module 15, (5) step 350: upon the authentication of the fingerprint image is recognized enabling the second light-emitting element 13 to emit the visible light VL to the finger 2, and receiving the second photo intensity signal IS2 of the invisible light IL and the visible light VL reflected from the finger 2 by the photoelectron sensor module 11, (6) step 360: converting the second photo intensity signal IS2 to the second photocurrent signal PS2 by the photoelectron sensor module 11 and delivering the second photocurrent signal PS2 to the analog/digital converting module 14, (7) step 370: converting the second photocurrent signal PS2 to the second digital signal DS2 by the analog/digital converting module 14, and (8) step 380: outputting the finger oxygen saturation image by the processor module 15 on basis of the second digital signal DS2 to determine whether the real finger is placed.

The method embodiment in FIG. 5 may drive the first light-emitting element 12 to emit the invisible light IL to the finger 2 and perform the corresponding photoelectron conversions through the analog/digital converting module 14 and the processor module 15 for obtaining the fingerprint image. When the obtained fingerprint image could be considered authentic, the method may further drive the second light-emitting element 13 to emit the visible light VL to the finger 2 to obtain the finger oxygen saturation image before confirming whether the real finger is placed.

In view of above, the fingerprint identification apparatus according to the present disclosure may rely on the photoelectron sensor module to receive the invisible light penetrated inside and then reflected from the finger so as to distinguish the first photo intensity signal associated with the fingerprint valley from the first photo intensity signal associated with the fingerprint ridge. The photoelectron sensor module may convert the first photo intensity signals of distinct intensity before the analog/digital converting module may convert the first photo current signals corresponding to the first photo intensity signals that are different in intensity to the first digital signals. The processing module may receive the first digital signals and process the same before generating the fingerprint images reflective of the fingerprint valley and the fingerprint ridge.

When the visible light is emitted upon the finger, the absorption rates of the invisible light when penetrating into the finger for oxygenated hemoglobin and de-oxy hemoglobin are different, resulting in the different second photo intensity signals in terms of the intensity. The photoelectron sensor module may convert the second photo intensity signals into the corresponding second digital signals indicative of the different absorption rate. The processor module upon the receipt of the second digital signals may process the same to obtain the finger oxygen saturation images reflecting the different oxygen saturations.

Because of the photoelectron sensor module being compact as one of its advantages, the fingerprint identification apparatus of the present disclosure may be incorporated into the portable devices. Thus, the present disclosure may over the applicability challenge facing the conventional fingerprint identification apparatus, which is typically cumbersome. By simultaneously identifying the fingerprint image and the oxygen saturation image, whether the real finger is placed for the identification may be confirmed. Accordingly, any fake finger reflecting no oxygen saturation may not be used to get around the fingerprint identification apparatus according to the present disclosure.

Some modifications of these examples, as well as other possibilities will, on reading or having read this description, or having comprehended these examples, will occur to those skilled in the art. Such modifications and variations are comprehended within this disclosure as described here and claimed below. The description above illustrates only a relative few specific embodiments and examples of the present disclosure. The present disclosure, indeed, does include various modifications and variations made to the structures and operations described herein, which still fall within the scope of the present disclosure as defined in the following claims.

What is claimed is:

1. A fingerprint identification apparatus capable of simultaneously identifying a fingerprint image and oxygen saturation to identify fingerprint pattern and blood oxygen of a finger, comprising: a first light-emitting element to emit an invisible light to the finger; a second light-emitting element to emit a visible light to the finger; a photoelectron sensor module having a light reception surface on which the finger is placed, the photoelectron sensor module receiving a first photo intensity signal of the invisible light reflected from the finger and converting the first photo intensity signal to a first photocurrent signal, and the photoelectron sensor module receiving a second photo intensity signal of the invisible light reflected from the finger and converting the second photo intensity signal to a second photocurrent signal; an analog/digital converting module electrically connected to the photoelectron sensor module, for converting the first photocurrent signal to a first digital signal and converting the second photocurrent signal to a second digital signal; and a processor module electrically connected to the analog/digital converting module for outputting a fingerprint image corresponding to the first digital signal to be recognized and outputting a finger oxygen saturation image corresponding to the second digital signal to be recognized.

2. The apparatus according to claim 1, wherein the photoelectron sensor module is composed by photoelectron sensing elements arranged in array, the photoelectron sensing elements comprise multiple visible light sensors and multiple invisible light sensors, and the visible light sensors and the invisible light sensors are adjacently arranged to define the light reception surface.

3. The apparatus according to claim 2, further comprising scattering medium covering the light reception surface of the photoelectron sensor module with the scattering medium allowing for the contact by the finger.

4. The apparatus according to claim 1, further comprising a functionality circuit board on which the first light-emitting element and the second light-emitting element are electrically disposed with the first light-emitting element and the second light-emitting element adjacently disposed to surround the photoelectron sensor module.

5. The apparatus according to claim 4, wherein the analog/digital converting module and the processor module are selectively electrically disposed on the functionality circuit board or a portable electronic device.

6. A fingerprint identification method capable of simultaneously identifying a fingerprint image and oxygen saturation, comprising: allowing for a finger to be placed on a light reception surface of an photoelectron sensor module; enabling a first light-emitting element to emit an invisible light to the finger and enabling a second light-emitting element to emit a visible light to the finger; receiving a first light intensity signal corresponding to the invisible light penetrated into the finger and then reflected by the finger using the photoelectron sensor module and receiving a second light intensity signal corresponding to the visible light reflected from the finger using the photoelectron sensor module; converting the first light intensity signal to a first photocurrent signal by the photoelectron sensor module, converting the second light intensity signal to a second photocurrent signal by the photoelectron sensor module, and delivering the first photocurrent signal and the second photocurrent signal to an analog/digital converting module by the photoelectron sensor module; converting the first photocurrent signal to a corresponding first digital signal by the analog/digital converting module, converting the second photocurrent signal to a corresponding second digital signal by the analog/digital converting module, and delivering the first digital signal and the second digital signal to a processor module by the analog/digital converting module; and outputting a fingerprint image corresponding to the first digital signal by the processor module, outputting a finger oxygen saturation image corresponding to the second digital signal by the processor module, and recognizing the fingerprint image and the finger oxygen saturation image by the processor module.

7. The method according to claim 6, wherein the processor module further comprises a fingerprint recognition program, an oxygen saturation recognition program, and an image certification program, further comprising: processing the first digital signal by the fingerprint identification program to prepare the fingerprint image; processing the second digital signal by the oxygen saturation recognition program to prepare the finger oxygen saturation image; and certifying the fingerprint image to confirm user identity with the image certification program and confirming whether a real finger is placed according to the finger oxygen saturation image by the image certification program.

8. A fingerprint identification method capable of simultaneously identifying a fingerprint image and oxygen saturation, comprising: allowing for a finger to be placed on a light reception surface of a photoelectron sensor module; enabling a first light-emitting element to emit an invisible light to the finger; receiving a first light intensity signal corresponding to the invisible light penetrated into the finger and then reflected by the finger using the photoelectron sensor module; converting the first light intensity signal to a first photocurrent signal by the photoelectron sensor module and converting the first photocurrent signal to a corresponding first digital signal by an analog/digital converting module; processing the first digital signal to prepare a fingerprint image to be recognized by a processor module and upon the authentication of the fingerprint image is recognized enabling a second light-emitting element to emit a visible light to the finger, and receiving a second photo intensity signal of the visible light reflected from the finger by the photoelectron sensor module; converting the second photo intensity signal to a second photocurrent signal by the photoelectron sensor module and delivering the second photocurrent signal to the analog/digital converting module; converting the second photocunent signal to a second digital signal by the analog/digital converting module; and outputting a finger oxygen saturation image by the processor module on basis of the second digital signal to determine whether a real finger is placed.

9. The method according to claim 8, wherein the processor module further comprises a fingerprint recognition program, an oxygen saturation recognition program, and an image certification program, further comprising: processing the first digital signal by the fingerprint identification program to prepare the fingerprint image; processing the second digital signal by the oxygen saturation recognition program to prepare the finger oxygen saturation image; and certifying the fingerprint image to confirm user identity with the image certification program and confirming whether the real finger is placed according to the finger oxygen saturation image by the image certification program.

* * * * *